United States Patent [19]

Maeda et al.

[11] Patent Number: 5,100,702

[45] Date of Patent: Mar. 31, 1992

[54] THIN PLATINUM FILM-FORMING COMPOSITION

[75] Inventors: Koichi Maeda; Ryozo Sakoda; Hideki Takamatsu, all of Funabashi, Japan

[73] Assignee: Nissan Chemical Industries, Ltd., Tokyo, Japan

[21] Appl. No.: 656,880

[22] Filed: Feb. 19, 1991

[30] Foreign Application Priority Data

Feb. 22, 1990 [JP] Japan .................................. 2-42243

[51] Int. Cl.$^5$ .................................................. B05D 3/02
[52] U.S. Cl. .................................. 427/229; 427/126.5; 106/1.28; 556/136
[58] Field of Search .................. 106/1.28; 427/229; 556/136

[56] References Cited

U.S. PATENT DOCUMENTS 4,098,807 7/1978 Stone et al. .................. 260/420 CY
4,631,310 12/1986 Chandra et al. .................. 524/862

FOREIGN PATENT DOCUMENTS 1535717 12/1978 United Kingdom .

OTHER PUBLICATIONS

Boag et al., "Alkyne Complexes of Platinum Part 3, The Synthesis and Crystal Structure of bis(Diphenylacetylene) Platinum and Studies on Related Compounds" J. Chem. Soc., Dalton Trans., (11), (1986), pp. 2170–2180.

*Primary Examiner*—William R. Dixon, Jr.
*Assistant Examiner*—Margaret V. Einsmann
*Attorney, Agent, or Firm*—Oliff & Berridge

[57] ABSTRACT

A thin platinum film is formed on a substrate of glass, alumina or pottery by applying on the surface of the substrate a solution containing one part by weight of an organic platinum complex represented by formula (I):

$$PT(R^1-C\equiv C-R^2)_2 \qquad (I)$$

wherein $R^1$ and $R^2$ each represents a group of phenyl, 4-methylphenyl or 4-methoxyphenyl and 0.1 to 100 parts by weight of an organic solvent dissolving the complex, then heating the coated film at the decomposition temperature of the complex and thereafter firing the film and 400° to 900° C.

4 Claims, No Drawings

THIN PLATINUM FILM-FORMING COMPOSITION

FIELD OF THE INVENTION

The present invention relates to an improvement in a method of forming a thin film of platinum on a heat resistant substrate by applying a coating paste containing an organic platinum compound on said substrate and heating the film to form metallic platinum, and more precisely to a coating paste containing a specific organic platinum complex and an organic solvent dissolving said complex in high concentration to be used therein. The thin film of platinum produced on the substrate shows electroconductivity and can be used in various fields, such as for example, electric or electronic circuits and electrodes.

BACKGROUND OF THE INVENTION

As a means of forming a thin film of a metal platinum, heretofore, there has been known a method of coating a platinum paste of a so-called liquid platinum, which consists essentially of a reaction product of a balsam sulfide and a platinum halide, on a substrate followed by heating it to form a thin platinum film on the substrate.

As examples of other platinum pastes, JP-A-64-177 mentions a platinum alkyl mercaptide; JP-A-64-178 mentions a platinum pinene mercaptide; and JP-A-64-179 mentions a platinum essential oil mercaptide-containing composition. (The term "JP-A" as used herein means an "unexamined published Japanese patent application".)

JP-A-51-86451 mentions a method of coating a bis(-cis,cis-cycloocta-1,5-diene) platinum solution on a carrier followed by heating the carrier so as to decompose bis(cis,cis-cycloocta-1,5-diene) platinum on the carrier to thereby deposit a metal platinum on the same.

It further mentions a method of coating an organic platinum complex of a general formula (II):

$$Pt(Q)_3 \qquad (II)$$

where Q represents a compound having at least one olefinic double bond or acetylenic triple bond, such as an olefin, an allene, an acetylene or a substituted olefin, on a carrier followed by heating the carrier so as to decompose the compound of the above-mentioned formula (II) to thereby deposit a metal platinum on the same.

In the above-mentioned method of using a paste consisting essentially of a reaction product of a balsam sulfide and a platinum halide which contains a large number of sulfur atoms and halogen atoms, a large amount of corrosive gases of sulfur oxides, halogens or hydrogen halides are generated during heating of the carrier for forming the platinum coat. As a result, the thus generated corrosive gases would corrode the firing furnace. Additionally, where a thin film of a metal which is easily corroded by such gases, such as silver or the like, has already been formed on the substrate, the thin film would also be corroded.

Regarding the methods illustrated in the above-mentioned JP-A-64-177, 64-178 and 64-179, all the compounds which are used as a platinum source contain sulfur atom and therefore generate also a large amount of corrosive sulfur oxides during heating of the coated film.

Regarding the method as illustrated in the above-mentioned JP-A-51-86451, in which a bis(cis,cis-cycloocta-1,5-diene) platinum solution is coated on a carrier and thereafter the thus coated carrier is heated so as to deposit a platinum metal on the carrier, a paste having a high concentration could not be obtained as the solubility of bis(cis,cis-cycloocta-1,5-diene)platinum to the solvent is low. Therefore, there is a limitation on the elevation of the content of platinum in the solution to be coated and, as a result, the thickness of the platinum film to be coated is naturally limited. In addition, selection of additives which are added to the coating solution for the purpose of improving the coatability of the solution and of improving the adhesiveness between the platinum film formed and the carrier, as well as the amount of such additives to be added are also extremely limitative, in carrying out the method. A satisfactory thin film of platinum metal could not be obtained from a solution of bis(cis,cis-cycloocta-1,5-diene)platinum. Regarding the other method as illustrated in the same JP-A-51-86451, in which a compound of the above-mentioned general formula (II) is coated on a substrate and thereafter the thus coated substrate is heated so as to decompose the compound of the formula (II) to thereby deposit a platinum on the substrate, a paste having a constant quality could not be obtained since the solution of the compound of the above-mentioned formula (II) is unstable and the solution is easily decomposed during storage even at room temperature. The published specification of JP-A-51-86451 is silent on the solubility of bis(cis,cis-cycloocta-1,5-diene) platinum and that of platinum compounds of the above-mentioned general formula (II), and it is also silent on a paste containing the above-mentioned platinum compound for forming a thin film of a metal platinum by pyrolysis. Additionally, it does not refer to platinum complexes of a type containing two Q's as ligands.

In particular, in the technical field of forming electroconductive circuits on a substrate, a method where a solution of an organic platinum compound is coated on a substrate and thereafter the coated film is heated and fired to form such an electroconductive thin film that having a thickness of about 0.1 to 1 micron is desired.

SUMMARY OF THE INVENTION

Under the situation, the object of the present invention is to provide a thin platinum film-forming composition, which may give a uniform and continuous thin platinum film on a substrate by an industrially advantageous method and which does not contain disadvantageous atoms to cause generation of corrosive gases, such as halogen atoms and sulfur atom, and also to provide a method of forming a thin platinum film by the use of the composition.

Specifically, the present invention provides a thin platinum film-forming composition comprising an organic solvent solution containing from 1 to 91 % by weight of an organic platinum complex of a general formula (I):

$$Pt(R^1-C\equiv C-R^2)_2 \qquad (I)$$

Where $R_1$ and $R_2$ each represent a group of phenyl, 4-methylphenyl or 4-methoxyphenyl.

The present invention further provides a method of forming a platinum film on a substrate, in which the above-mentioned thin platinum film-forming composition is coated on the surface of a heat-resistant substrate, then heated with avoiding boiling of the coated composition and fired at 400° to 900° C.

DETAILED DESCRIPTION OF THE INVENTION

Compounds of the above-mentioned general formula (I) which are used in the present invention can be prepared, for example, in accordance with the method described in J. C. S. Dalton, 1980, 2170 to 2181, in which bis(cis,cis-cycloocta-1,5-diene) platinum is reacted with two molar times or more, to the platinum complex compound, of an acetylene compound corresponding to the group of $R^1$—C≡C—$R^2$ (where $R^1$ and $R^2$ have the same meanings as mentioned above) in the above-mentioned formula (I) in an inert solvent such as petroleum ether.

As examples of compounds of the above-mentioned formula (I) which are used in the present invention, the following are referred to:
Bis[diphenylacetylene]platinum
Bis[di(4-methylphenyl)acetylene]platinum
Bis[di(4-methoxyphenyl)acetylene]platinum
Bis[4-.methylphenylphenylacetylene]platinum.
Bis[4-methoxyphenylphenylacetylene]platinum.

As examples of organic solvents which may be used in the composition of the present invention, there are mentioned ketones such as methyl ethyl ketone and cyclohexanone; esters such as ethyl acetate, amyl acetate, benzyl acetate, dibutyl oxalate, dibutyl itaconate, benzyl benzoate, dibutyl phthalate, dioctyl phthalate and butylcarbitol acetate; ethers such as dioxane, ethyl cellosolve and dipentene oxide; alcohols such as butanol and cyclohexanol; aromatic hydrocarbons such as toluene and xylene; nitro-substituted aromatic hydrocarbons such as nitrobenzene and nitrotoluene; terpenes such as pinene and terpineol; essential oils such as lavender oil, linseed oil and rosemary oil; as well as mixtures of the above-mentioned substances.

The composition of the present invention is easily prepared as a solution, by blending the above-mentioned compound of formula (I) and the above-mentioned organic solvent, and further additives if desired.

The proportion of the above-mentioned compound of formula (I) to the above-mentioned organic solvent to be blended is preferably such that the solvent is from 0.1 to 100 parts by weight, especially preferably from 0.5 to 70 parts by weight, to one part by weight of the compound of formula (I).

For preparing a preferred composition of the present invention, it is desired to use organic solvents capable of uniformly dissolving the compounds of formula (I) at room temperature and to employ the blending proportion between the selected solvent and the compound of formula (I) to satisfy the condition of uniformly dissolving the compound in the solvent at room temperature. Any conventional coating method may be adopted for applying the composition of the present invention. For instance, known coating methods, such as brush-coating method, screen-printing method, relief-printing method, intaglio-printing method, lithographic-printing method, off set-printing method and dipping method, may be employed. The kind of the compound of formula (I) as well as the kind and amount of the above-mentioned solvent are properly selected, in order to obtain a composition which is applicable to anyone of the above-mentioned coating methods and which is suitable to the heating condition to be used in the selected coating method, and pertinent viscosity and concentration are imparted to the composition.

The composition of the present invention may be applied to general substrates, for example, various ceramic substrates such as glass, alumina and pottery substrates, as well as various metal substrates having a melting point of 400° C or higher.

After the composition of the present invention has been applied to such a substrate, the film of the composition as coated on the substrate is heated at a temperature of the decomposition temperature of the compound of formula (I) with avoiding boiling of the composition of the coated film and fired preferably at 400° to 900° C. over a period of about 5 to 60 minutes, whereby a thin film of a metal platinum is formed on the substrate. The thin film may be mirror-like when the substrate has even surface.

The organic platinum complex of the above-mentioned formula (I) which may be in the composition of the present invention are stable at a relatively high temperature and have a high solubility in the above-mentioned solvents.

Therefore, it is considered that where the composition of the present invention is coated and heated on a substrate, the coated composition could still be in a liquid state having a high viscosity even after almost all of the solvent has been removed therefrom, and the state could be maintained until completion of the decomposition of the compound of formula (I) in the composition to give a uniform and continuous thin platinum film on the substrate.

Additionally, the organic platinum complexes of the above-mentioned formula (I) which may be in the composition of the present invention do not sublime even under heat. Therefore, a thin platinum film of the same weight as that of the platinum as contained in the coated composition can be formed on the coated substrate.

Where the content of the above-mentioned solvent in the composition of the invention is less than 0.1 part by weight to one part by weight of the organic platinum complex compound of the above-mentioned formula (I), the composition would be too viscous to have a sufficient coatability.

Where the content of the solvent in the composition is more than 100 parts by weight to one part by weight of the organic platinum complex of formula (I), the composition of itself would have no radical problem as it could be concentrated after coated on a substrate, provided that the coated substrate is heated carefully. However, the composition containing the solvent of such a large amount is unfavorable since the handlability and processability of the composition is to be poor. Additionally, as it has a small platinum metal content, the thin film to be formed would be too thin and would therefore easily be cracked.

Next, the present invention will be explained in more detail by way of the following examples and comparative examples, which, however, are not intended to restrict the scope of the present invention.

EXAMPLE 1

0.5 g of terpineol was added to 1 g of bis[diphenylacetylene]platinum at room temperature to obtain a uniform solution. The solution was coated on a glass substrate with a brush, then the substrate was heated from room temperature up to 400° C. over a period of about 15 minutes, and thereafter it was fired at 400° C. for 15 minutes. As a result, a smooth mirror-like thin platinum metal film was formed uniformly on all the part of the glass substrate as coated with the composition, the adhesion of the film to the substrate being firm.

EXAMPLE 2

80 g of terpineol was added to 1 g of bis[diphenylacetylene]platinum at room temperature to obtain a uniform solution. The solution was coated on a glass substrate with a brush, then the substrate was heated from room temperature up to 400° C. over a period of about 30 minutes, and thereafter it was fired at 400° C. for 15 minutes. As a result, a smooth mirror-like thin platinum metal film was formed uniformly on all the part of the glass substrate as coated with the composition, the adhesion of the film to the substrate being firm.

EXAMPLE 3

0.5 g of terpineol was added to 1 g of bis[diphenylacetylene]platinum at room temperature to obtain a uniform solution. The solution was coated on an alumina substrate with a brush, then the substrate was heated from room temperature up to 800° C. over a period of about 30 minutes, and thereafter it was fired at 800° C. over a period of about 30 minutes, and thereafter fired at 800° C. for 10 minutes. As a result, a smooth thin platinum metal film was formed uniformly on all the part of the alumina substrate as coated with the composition, the adhesion of the film to the substrate being firm.

EXAMPLE 4

0.5 g of toluene was added to 1 g of bis[diphenylacetylene]platinum at room temperature to obtain a uniform solution. The solution was coated on an alumina substrate with a brush, then the substrate was heated from room temperature up to 800° C. over a period of about 30 minutes, and thereafter fired at 800° C. for 10 minutes. As a result, a smooth thin platinum metal film was formed uniformly on all the part of the alumina substrate as coated with the composition, the adhesion of the film to the substrate being firm.

EXAMPLE 5

2.0 g of terpineol was added to 1 g of bis[diphenylacetylene]platinum at room temperature to obtain a uniform solution. The solution was coated on an alumina substrate with a brush, then the substrate was heated from room temperature up to 800° C. over a period of about 30 minutes, and thereafter it was fired at 800° C. for 10 minutes. As a result, a smooth thin platinum metal film was formed uniformly on all the part of the alumina substrate as coated with the composition, the adhesion of the film to the substrate being firm.

EXAMPLES 6 TO 15

The same process as in Example 5 was repeated, except that different combinations as indicated in Table below were used. As a result, a smooth thin platinum metal film was formed uniformly on all the part of the alumina substrate as coated with the composition in every combination, the adhesion of the film to the substrate being firm.

| | Compound | Solvent |
| --- | --- | --- |
| Example 6 | Bis[di(4-methylphenyl)acetylene] | Terpineol |

-continued

| | Compound | Solvent |
| --- | --- | --- |
| Example 7 | Platinum Bis[di(4-methoxyphenyl)acetylene] Platinum | Terpineol |
| Example 8 | Bis[diphenylacetylene]Platinum | Methyl ethyl ketone |
| Example 9 | Bis[diphenylacetylene]Platinum | Benzyl acetate |
| Example 10 | Bis[diphenylacetylene]Platinum | Dioctyl phthalate |
| Example 11 | Bis[diphenylacetylene]Platinum | Butyl carbitol acetate |
| Example 12 | Bis[diphenylacetylene]Platinum | Ethyl cellosolve |
| Example 13 | Bis[diphenylacetylene]Platinum | Xylene |
| Example 14 | Bis[diphenylacetylene]Platinum | Nitrobenzene |
| Example 15 | Bis[diphenylacetylene]Platinum | Rosemary oil |

COMPARATIVE EXAMPLE 1

The same process as in Example 1 was repeated except that 0.5 g of terpineol was added to 1 g of bis[cis,-cis-cycloocta-1,5-diene]bis[platinum at room temperature, in place of diphenylacetylene]platinum. However, the complex did not almost dissolve in the solvent. Then, 75.5 g of terpineol was further added thereto to form a uniform solution. The resulting solution was coated on a glass substrate with a brush and the coated substrate was heated from room temperature up to 400° C. over a period of about 30 minutes. In the process, however, brown fine grains were formed at the point when the substrate reached to about 100° C. so that the coated film became uneven. After further firing at 400° C. for 15 minutes, a fine powdery platinum metal was merely formed but any thin platinum metal film was not formed thereon.

COMPARATIVE EXAMPLE 2

The same process as in Example 4 was repeated except that 0.5 g of toluene was added to 1 g of bis[.cis,cis-cycloocta-1,5-diene]platinum at room temperature, in place of bis[diphenylacetylene]platinum. However, the complex did not almost dissolve in the solvent. Then, 75.5 g of toluene was further added thereto to form a uniform solution. The resulting solution was coated on a glass substrate with a brush and the coated substrate was heated from room temperature up to 400° C. over a period of about 30 minutes. In the process, however, brown fine grains were formed at the point when the substrate reached to about 80° C. so that the coated film became uneven. After further firing at 400° C. for 15 minutes, a fine powdery platinum metal was merely formed on the glass substrate but any thin platinum metal film was not formed thereon.

The composition of the present invention may be coated on a substrate such as a ceramic or metal substrate by any conventional method and may be heated also by any conventional method, whereby a uniform, continuous and thin film of a metal platinum is formed on the substrate with high adhesion between the film and the substrate.

In particular, since the composition of the present invention contains neither sulfur atom nor halogen atoms and therefore does not release any corrosive gas of sulfur oxides, halogens or hydrogen halides during pyrolysis thereof, it may well be applied on a substrate as previously coated with a thin film of a metal such as silver, which is easily corroded with a corrosive gas, to form a uniform, continuous and thin film of a metal platinum thereon. Additionally, the composition has further advantage that it does not corrode the firing furnace to be used for forming the substrate as coated with the composition and is free from environmental pollution in industrial use thereof.

Furthermore, as the composition does not lose the platinum metal content by sublimation even under heat, it is economically advantageous. Further, using the composition, a thin platinum film having a constant size and a constant thickness may easily be formed.

The composition of the present invention as well as a paste composition containing the same is especially advantageous for forming various thin film decorations of a platinum metal on a substrate, or for forming various electric or electronic circuits of thin films of a platinum metal on a substrate, or for forming various electrodes of thin films of a platinum metal on a substrate.

While the invention has been described in detail and with reference to specific embodiments thereof, it will be obvious to one skilled in the art that various changes and modifications can be made therein without departing from the spirit and scope thereof.

What is claimed is:

1. A method of forming a platinum film on a heat resistant substrate selected from the group consisting of glass, alumina and pottery, comprising coating the surface of the substrate with a solution containing one part by weight of an organic platinum complex represented by formula (I):

$$Pt(R^1-C\equiv C-R^2)_2 \qquad (I)$$

wherein $R^1$ and $R^2$ each represents a group of phenyl, 4-methylphenyl or 4-methoxyphenyl group and 0.1 to 100 parts by weight of an organic solvent dissolving said complex, then heating the coated film at the decomposition temperature of the complex and thereafter firing the film at 400° to 900° C.

2. The method of forming a platinum film on a heat resistant substrate as claimed in claim 1, in which the solution contains one part by weight of the organic platinum complex represented by formula (I) and 0.5 to 70 parts by weight of said organic solvent dissolving said complex.

3. The method of forming a platinum film on a heat resistant substrate as claimed in claim 1, in which the organic solvent is methyl ethyl ketone, cyclohexanone, ethyl acetate, amyl acetate, benzyl acetate dibutyl oxalate, dibutyl itaconate, benzyl benzoate, dibutyl phthalate, dioctyl phthalate, butylcarbitol acetate, dioxane, ethyl cellosolve, dipentene oxide, butanol, cyclohexanol, toluene, xylene, nitrobenzene, nitrotoluene, pinene, terpineol, lavender oil, linseed oil or rosemary oil.

4. The method of forming a platinum film on a heat resistant substrate as claimed in claim 1, in which the organic platinum complex is bis[diphenylacetylene]-platinum or bis[di(4-methoxyphenyl)acetylene]-platinum.

* * * * *